United States Patent [19]

Hiraoka et al.

[11] 4,017,488

[45] Apr. 12, 1977

[54] PROCESS FOR PREPARING 7β-ACYLAMINO-7α-ALKOXYCEPHALOS-PORINS

[75] Inventors: Tetsuo Hiraoka; Yukio Sugimura, both of Tokyo, Japan

[73] Assignee: Sankyo Company Limited, Tokyo, Japan

[22] Filed: July 29, 1975

[21] Appl. No.: 600,083

[30] Foreign Application Priority Data

Aug. 22, 1974 Japan .............................. 49-96495

[52] U.S. Cl. ............................ 260/243 C; 424/246
[51] Int. Cl.² ..................................... C07D 501/02
[58] Field of Search ............................... 260/243 C

[56] References Cited

UNITED STATES PATENTS 3,843,641  10/1964  Christensen et al. .......... 260/243 C
3,867,379  3/1975  Dolfini et al. .................. 260/243 C Primary Examiner—Nicholas S. Rizzo
Attorney, Agent, or Firm—Flynn & Frishauf

[57] ABSTRACT

A 7β-acylamino-7α-alkoxycephalosporin is prepared by reacting a 7-acylaminocephalosporin with a halogenating agent to give an iminohalide, reacting the latter compound with a base to give a keteneimine, reacting the latter compound with a halogen to give an α-halogeno iminohalide, reacting the latter compound with an alkali metal alkoxide and consecutively either subjecting the resulting compound to hydrolysis, or reacting the resulting compound with an acid or a halogenosilyl compound followed by treating the resulting compound with water.

The 7β-acylamino-7α-alkoxycephalosporin is useful as an antibacterial agent.

7 Claims, No Drawings

PROCESS FOR PREPARING 7β-ACYLAMINO-7α-ALKOXYCEPHALOSPORINS

This invention relates to a novel process for preparing a compound having the formula

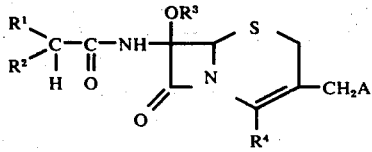

wherein R' represents hydrogen atom, cyano group, an alkoxycarbonyl group, an acylamino group, an alkoxycarbonylamino group, an optionally substituted - alkyl group, - alkenyl group, - alkynyl group, - aryl group, - aralkyl group, - alkylthio group, - alkenylthio group, - alkynylthio group, - arylthio group, - aralkylthio group, - carbamoyl group, - alkylsulfonyl group or - aminosulfonyl group; $R^2$ represents hydrogen atom, cyano group, an alkoxycarbonyl group, an optionally substituted - alkyl group, - alkenyl group, - alkynyl group, - aryl group, - aralkyl group, - alkylthio group, alkenylthio group, - alkylthio group, - arylthio group, - aralkylthio group, - alkyloxy group, - alkenyloxy group, - alkynyloxy group, - aryloxy group, - aralkyloxy group, - heterocyclic group, - heterocyclic oxy group, - heterocyclic thio group or - alkylsulfonyl group; $R^3$ represents a lower alkyl group or an optionally substituted aralkyl group; $R^4$ represents carboxyl group or a protected carboxyl group, A represents hydrogen, azido or the formula -B-E in which B is oxygen or sulfur and E is acyl, lower alkyl, having 1-4 carbon atoms optionally substituted-carbamoyl, -thiocarbamoyl or -heterocyclic group.

In the above formula (I), $R^1$ is preferably hydrogen atom, an alkyl group having 1 - 4 carbon atoms, e.g., methyl, ethyl, n-propyl, isopropyl or n-butyl, or an aryl group, e.g., phenyl or naphthyl; $R^2$ is preferably hydrogen atom, an alkyl group having 1 - 4 carbon atoms, e.g., methyl, ethyl, n-propyl, isopropyl, n-butyl, isobutyl or tert-butyl, an aryl group, e.g., phenyl or naphthyl, an alkylthio group having 1 - 4 carbon atoms, e.g., methylthio, ethylthio, n-propylthio or isopropylthio, an alkynylthio group having 2 - 4 carbon atoms, e.g., propargylthio, an arylthio group, e.g., phenylthio, an azidoalkylthio group having 1 - 4 carbon atoms, e.g., azidomethylthio or azidoethylthio, a cyanoalkylthio group having 1 - 4 carbon atoms in the alkyl moiety, e.g., cyanomethylthio or cyanothylthio, an alkylsulfonyl group having 1 - 4 carbon atoms, e.g., methylsulfonyl or ethylsulfonyl, a 5- or 6-membered heterocyclic thio group containing one or more of sulfur, nitrogen and/or oxygen atom in the ring which may be substituted with a lower alkyl group having 1 - 3 carbon atoms, e.g., imidazolythio, thiadiazolylthio, triazolythio, thienylthio, isoxazolylthio, methylisoxazolylthio, tetrazolylthio, methyltetrazolylthio, pyrimidinylthio or pyridylthio, a 5- or 6-membered heterocyclic oxy group containing one or more of sulfur, nitrogen and/or oxygen atom in the ring which may be substituted with a lower alkyl group having 1 - 3 carbon atoms, e.g., isoxazolyloxy, methylisoxazolyloxy, imidazolyloxy, thiadiazolyloxy, triazolyloxy, thienyloxy, tetrazolyloxy, methyltetrazolyloxy, pyrimidinyloxy, or pyridyloxy, a 5- or 6-membered heterocyclic group containing one or more of sulfur, nitrogen and/or oxygen atom in the ring which may be substituted with a lower alkyl group having 1 - 3 carbon atoms, e.g., thienyl, imidazolyl, thiadiazolyl, isoxazolyl, methylisoxazolyl, tetrazolyl, methyltetrazolyl, pyrimidinyl or a pyridyl, and alkylsulfonyl group having 1 - 4 carbon atoms, e.g., methylsulfonyl, ethylsulfonyl or n-propylsulfonyl; $R^3$ is preferably an alkyl group having 1 - 4 carbon atoms, e.g., methyl, ethyl, n-propyl, isopropyl or n-butyl; $R^4$ is carboxyl group or a protected carboxyl group such as an alkoxycarbonyl group having 1 - 4 carbon atoms in the alkyl moiety, e.g., methoxycarbonyl, ethoxycarbonyl, n-propoxycarbonyl or n-butoxycarbonyl, a halogenoalkoxycarbonyl group having 1 - 4 carbon atoms in the alkyl moiety, e.g., dichloroethoxycarbonyl or trichloroethoxycarbonyl, a benzyloxycarbonyl group optionally substituted with halogen, methoxy or nitro, e.g., benzyloxycarbonyl, p-chlorobenzyloxycarbonyl, p-methoxy benzyloxycarbonyl or p-nitro-benzyloxycarbonyl, diphenylmethyloxycarbonyl group, a trialkylsilyloxycarbonyl group having 1 - 4 carbon atoms in each alkyl moiety, e.g., trimethylsilyloxycarbonyl or triethylsilyloxycarbonyl, a dialkylhalogenosilyloxycarbonyl group having 1 - 4 carbon atoms in each alkyl moiety, e.g., dimethylchlorosilyloxycarbonyl or dimethylbromosilyoxycarbonyl, a phenacyloxycarbonyl group optionally substituted with halogen, or methoxy, e.g., p-chlorophenacyloxycarbonyl, p-bromophenacyloxycarbonyl, p-methoxyphenacyloxycarbonyl or an acyloxycarbonyl, e.g., acetoxycarbonyl or benzoyloxycarbonyl, a halogenoacylcarbonyl group, e.g., chloroacetoxycarbonyl or bromoacetoxycarbonyl, a dihalogenophosphinooxycarbonyl group, e.g., dichlorophosphinooxycarbonyl or dibromophosphinooxycarbonyl, a dialkylphosphinoxycarbonyl group, e.g., dimethylphosphinoxycarbonyl or an aminocarbonyl group, e.g., 3-oxo-2,3-dihydro-s-triazolo[4,3-a]pyridone-3-ylcarbonyl or saccharylcarbonyl; E is preferably an acyl group, e.g., acetyl, propionyl or benzoyl, carbamoyl group or a 5- or 6-membered heterocyclic group, which may be substituted with a lower alkyl group having 1 - 3 carbon atoms, e.g., tetrazolyl, 1-methyltetrazolyl, isoxazolyl, imidazolyl, thiazolyl, triazolyl, thienyl, thiadiazolyl, methylthiadiazolyl, pyrimidinyl or pyridyl.

Heretofore, there have been known various processes for introducing an alkoxy group into the 7-position of cephem ring, of which the alkoxylation with t-butylhypochlorite and lithium alkoxide is the simplest to perform and gives the best yield [R. A. Firestone and B. G. Christensen, J. Org. Chem. 38, 1436 (1973); G. A. Koppel and R. E. Koehler, J. Amer. Chem. Soc. 95, 2403 (1973)]. However, this method has the disadvantage that it is not applicable in the case of cephalosporins which are sensitive to t-butylhypochlorite, namely, those which have an anion formation center in the side chain.

It is thus an object of the present invention to provide a novel and generally applicable process for preparing the 7β-acylamino-7α-alkoxycephalosparine having the formula (I) which are valuable as antibacterial agents.

In accordance with the present invention, compounds having the formula (I) can be prepared by reacting a 7-acylaminocephalosporin having the formula:

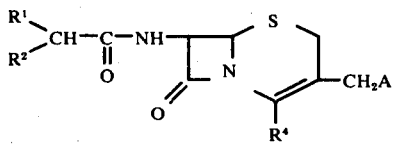

wherein $R^1$, $R^2$, $R^4$ and A have the same meanings as above with a halogenating agent to give an iminohalide having the formula:

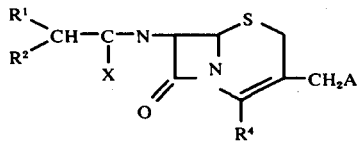

wherein X represents a halogen atom and $R^1$, $R^2$, $R^4$ and A have the same meanings as above, reacting the latter compound with a base to obtain a keteneimine having the formula:

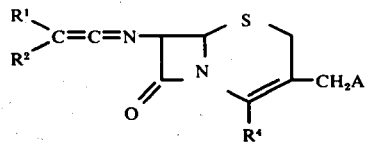

wherein $R^1$, $R^2$, $R^4$ and A have the same meanings as above, reacting the latter compound with a halogen to obtain a α-halogeno-iminohalide having the formula:

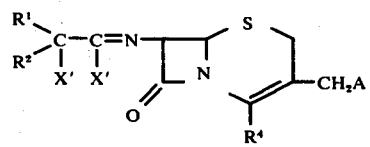

wherein $R^1$, $R^2$, $R^4$ and A have the same meanings as above and X' represents a halogen atom, treating the latter compound with an alkali metal alkoxide having the formula:

$R^3$ OM wherein M represents an alkali metal and $R^3$ has the same meaning as above
and consecutively either subjecting the resulting compound to hydrolysis, or reacting the resulting compound with an acid or a halogenosilyl compound followed by treating the resulting compound with water.

The 7α-alkoxy-7β-acylamidocephalosporin compounds having the formula (I) obtained by this invention are useful antibacterial agents.

The starting compounds having the formula (II) can be prepared by reacting the compounds having a free amino radical at the 7-position of the cephalosporin compound, for example, esters of 7-aminocephalosporanic acid, 7-aminodeacetoxycepharospolanic acid, 7-amino-3-(1-methyl-1H-tetrazol-5-yl)thiomethyl-cephem-4-carboxylic acid with a carboxylic acid having the formula

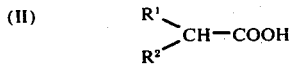

wherein $R^1$ and $R^2$ have the same meanings as above or its reactive derivative, for example, acid halide or acid anhydride in a known manner. There can also be used 7-acylaminocephalosporins, obtained by fermentation such as cephalosporin C, as starting materials. The acylamino radical in the 7-position of the starting cephalosporin can be α- or β-configuration.

The first step of this invention is carried out by reacting the compounds having the formula (II) with halogenating agents to give the iminohalide derivatives (III). This reaction can be carried out by reacting the starting material (II) with a halogenating agent in an inert solvent such as chloroform, methylenechloride dichloroethane, benzene and the like. As the halogenating agents, there may preferably be used phosphorus halide and halogenated sulfur compounds most favorably, phosphorus pentachloride, phosphorus pentabromide and thionyl chloride. This reaction can be carried out at a temperature of from −50° to 40° C, and a good result is obtained when it is carried out in the presence of an acid-binding reagent; quinoline, pyridine, organic tertiary amines and the like are usually used. To isolate the products obtained by this step, in cases where the products are stable to water and weak alkali, the products in an organic solvent are washed with a weak alkali solution and water; dried over sodium sulfate, and the solvent is distilled off to give the products which are practically pure.

Also, in case where the products obtained by this step are unstable to water, the solvent is distilled off from the reaction mixture under reduced pressure and the residue is dissolved in an inert solvent such as tetrahydrofuran, ether or benzene, and the amine salt resulting this reaction is filtered off. The products contained in the filtrate can be used for the next step without any operation.

The second step of this invention is carried out by treating the compounds having the formula (III) obtained by the above step with a base to obtain keteneimine derivatives (IV).

As the bases, there may preferably be used inorganic bases such as potassium carbonate, sodium carbonate, potassium hydroxide and sodium hydroxide and organic tertiary amines such as tri-loweralkyl amines aromatic amines, and stronger bases such as diazabicyclooctane, and diazabicyclononene. This reaction can be carried out in an inert solvent such as chloroform, tetrahydrofuran, ether or benzene at a temperature from −30° C to room temperature for 5 to 60 minutes. The amount of the base used is not limited but it is enough to use one molar amount or a slight excess amount. The products having the formula (IV) obtained above can be purified by diluting the reaction mixture with a water-immiscible organic solvent, washing with water, drying and distilling the solvent and, if necessary, treating the products with a usual chromatography. But as many of the products having the formula (IV) are generally unstable to water or acid except specified compounds, the reaction mixture per se is used for the next reaction.

This third step of this invention can be carried out by reacting the compounds (IV) with a halogen in an inert solution such as tetrahydrofuran, ether, toluene, chloroform, or methylenechloride. The preferable halogens are chlorine, bromine and iodine. The reaction is completed at a temperature of from −50° C to room temperature for 5 – 60 minutes. The amount of the halogen used is preferred to be 1 molar weight or slight excess.

The compounds (V) obtained above may be purified in the same manner as the compounds (III), but they are usually used for the next step without any isolation and purification.

The fourth step of this invention is carried out by reacting the α-halogeno-imino-halide having the formula (V) with the alkali metal alkoxyide having the formula $R^3OM$, wherein $R^3$ and M have the same meanings as above, to introduce an alkoxy radical into 7α-position of cephalosporin. The alkoxy-introducing reaction can be carried out by treating the compounds (V) with the alkali metal alkoxide in an inert solvent such as tetrahydrofuran, ether, chloroform or toluene at a temperature of from −78° ~ −15° C. The reaction is completed in 5 – 60 minutes and an alkoxy radical ($R^3O$) is introduced into the 7α-position.

Alkali metal alkoxyides $R^3OM$ are used in more than two equivalent amounts and the presence of a small amount of the corresponding alcohol ($R^3OH$ wherein $R^3$ has the same meaning as above) ends in a good result. The resulting compound is consecutively subjected to hydrolysis, or reaction with an acid or a halogenosilyl compound, and treating the resulting compound with water.

The hydrolysis proceeds in the presence of water, but it generally proceeds smoothly in the presence of an acid. This reaction can usually be completed by adding water or acid or its solution to the reaction mixture after the reaction with an alkali metal alkoxide is completed and carrying out the reaction at about room temperature for several hours to give 7α-alkoxy-7β-acylaminocephalosporin compounds. As the acid used in this reaction, there may be employed a mineral acid or an organic acid. There are preferably used hydrochloric acid, sulfuric acid, trifluoroacetic acid and trichloroacetic acid.

The reaction with acid and treatment with water can be carried out by adding a Lewis acid such as aluminium chloride or borontrifluoride-ether complex to the completed reaction mixture of the above step and subjecting it to reaction at room temperature. In this case, the presence of a tertiary amine such as quinoline and triethylamine gives a good result.

Reaction of a halogenosilyl compound and treatment of the resulting compound with water can be carried out by adding a lower alkyl-silyl halide such as trimethylchlorosilane, or dimethyldichlorosilane to the completed reaction mixture of the above step and causing them to react at room temperature and treating with water. In this case, the presence of a tertiary amine such as quinoline or triethylamine also gives a good result.

The compounds having the formula (I) obtained by the above method can be obtained by pouring the reaction mixture into water, extracting with an organic solvent, washing this extract with water, drying and distilling the solvent. The compounds can be purified by a usual chromatography, if necessary.

As the representative examples of the compounds having the formula (I), there can be mentioned as follows: 7β-propionamido-7α-methoxy-3-methyl-3-cephem-4-carboxylic acid, 7β-phenoxyacetamido-7α-methoxy-3-methyl-3-cephem-4-carboxylic acid, 7β-phenylthioacetamido-7α-methoxy-3-acetoxymethyl-3-cephem-4-carboxylic acid, 7β-(5-amino-5-carboxyvaleramido)-7α-methoxy-3-methoxy-3-acetoxymethyl-3-cephem-4-carboxylic acid, 7β-(1,2,4-triazol-4H-3-yl)thioacetamido-7α-methoxy-3-carbamoyloxymethyl-3-cephem-4-carboxylic acid, 7β-(imidazol-2-yl)thioacetamido-7α-methoxy-3-carbamoyloxymethyl-3-cephem-4-carboxylic acid, 7β-(1,3,4-thiadiazol-2-yl)thioacetamido-7α-methoxy-3-carbamoyloxy-3-cephem-4-carboxylic acid, 7β-propargylthioacetamido-7α-methoxy-3-carbamoyloxymethyl-3-cephem-4-carboxylic acid, 7β-cyanomethylthioacetamido-7α-methoxy-3-carbamoyloxy-methyl-3-cephem-4-carboxylic acid, 7β-(5-methyl-1,2,4-triazol-4H-3-yl)thioacetamido-7α-methoxy-3-carbamoyloxymethyl-3-cephem-4-carboxylic acid, 7β-(2-pyridyl)thioacetamido-7α-methoxy-3-carbamoyloxymethyl-3-cephem-4-carboxylic acid, 7β-(2-pyrimidyl)thioacetamido-7α-methoxy-3-carbamoyloxymethyl-3-cephem-4-carboxylic acid, 7β-(2-thiazolinyl)thioacetamido-7α-methoxy-3-carbamoyloxy-methyl-3-cephem-4-carboxylic acid, 7β-(n-propylthioacetamido)-7α-methoxy-3-carbamoyloxymethyl-3-cephem-4-carboxylic acid, 7β-cyanomethylthioacetamido-7α-methoxy-3-acetoxymethyl-3-cephem-4-carboxylic acid, 7β-(2-imidazolyl)thioacetamido-7α-methoxy-3-acetoxymethyl-3-cephem-4-carboxylic acid, 7β-(1,3,4-thiadiazolyl-2-yl)thioacetamido-7α-methoxy-3-(1-methyl-1H-tetrazol-5-yl)thiomethyl-3-cephem-4-carboxylic acid, 7β-(2-imidazolyl)thioacetamido-7α-methoxy-3-(1-methyl-1H-tetrazol-5-yl)thiomethyl-3-cephem-4-carboxylic acid, 7β-cyanomethylthio-acetamido-7α-methoxy-3-(1-methyl-1H-tetrazol-5-yl)thiomethyl-3-cephem-4-carboxylic acid, 7β-propargylthioacetamido-7α-methoxy-3-(1-methyl-1H-tetrazol-5-yl)thiomethyl-3-cephem-4-carboxylic acid and the like. There can be also mentioned the above cephalosporin derivatives, the carboxyl radicals of which are protected with a methyl, p-methoxybenzyl, bromophenacyl, benzhydryl, trimethylsilyl, 3-oxo-2,3-dihydro-s-triazolo[4,3-a]-pyridon-3-yl radical.

Particularly, the following compounds have excellent anti-bacterial activities against a broad range of disease germs: 7β-(imidazol-2-yl)thioacetamido-7α-methoxy-3-(1-methyl-1H-tetrazol-5-yl)thiomethyl-3-cephem-4-carboxylic acid, 7β-(1,3,4-thiadiazol-2-yl)thioacetamido-7α-methoxy-3-(1-methyl-1H-tetrazol-5-yl)thiomethyl-3-cephem-4-carboxylic acid, 7β-(3-isoxazolyloxy)acetamido-7α-methoxy-3(1-methyl-1H-tetrazol-5-yl)thiomethyl-3-cephem-4-carboxylic acid, 7β-propargylthioacetamido-7α-methoxy-3-(1-methyl-1-H-tetrazol-5-yl)thiomethyl-3-cephem-4-carboxylic acid, 7β-cyanomethylthioacetamido-7α-methoxy-3-(1-methyl-1H-tetrazol-5-yl)thiomethyl-3-cephem-4-carboxylic acid, 7β-(5-methyl-1,3,4-thiadiazol-2-yl)thioacetamido-7α-methoxy-3-(1-methyl-1H-tetrazol-5-yl)thiomethyl-3-cephem-4-carboxylic acid, 7β-(1,2,4-triazol-4H-3-yl)thioacetamido-7α-methoxy-3-carbamoyloxymethyl-3-cephem-4-carboxylic acid, 7β-(imidazol-2-yl)thioacetamido-7α-methoxy-3-carbamoyloxymethyl-3-cephem-4-carboxylic acid, 7β-(1,3,4-thiadiazol-2-yl)thioacetamido-7α-methoxy-3-carbamoyloxymethyl-3-cephem-4-carboxylic acid, 7β-(5-methyl-1,3,4-thiadiazol-2-yl)thioacetamido-7α-methoxy-3-carbamoyloxymethyl-3-cephem-4-carboxylic acid, 7β-propargylthioacetamido-7α-methoxy-3-carbamoyloxymethyl-3-cephem-4-carboxylic acid, 7β- cyanomethylthioacetamido-7α-methoxy-3-carbamoyloxymethyl-3-cephem-4-carboxylic acid, 7β-cyanomethylthioacetamido-7α-methoxy-3-acetoxymethyl-3-cephem-4-carboxylic acid, 7β-azidomethylthioacetamido-7α-methoxy-3-acetoxymethyl-3-cephem-4carboxylic acid, 7β-(1,3,4-thiadiazol-2-yl)thioacetamido-7α-methoxy-3-acetoxymethyl-3-cephem-4-carboxylic acid, 7β-propargylthioacetamido-7α-methoxy-3-acetoxymethyl-3-cephem-4-carboxylic acid, 7β-(imidazol-2-yl)thioacetamido-7α-methoxy-3-acetoxymethyl-3-cephem-4-carboxylic acid, 7β-(3-isoxazolyloxy)acetamido-7α-methoxy-3-acetoxymethyl-3-cephem-4-carboxylic acid, and 7β-(3-isoxazolyl)-thioacetamido-7α-3-acetoxymethyl-3-cephem-4-carboxylic acid.

The antimicrobial activities of these compounds can be summarized in the following Table:

Table

| | Minimal inhibitory concentrations of various microorganisms mcg/ml | | | | | | | | |
|---|---|---|---|---|---|---|---|---|---|
| | I* | | II | | III | IV | | V | VI |
| Tested compounds | A | B | A | B | | A | B | | |
| 7β-(imidazol-2-yl)thioacetamido-7α-methoxy-3-(1-methyl-1H-tetrazol-5-yl)thiomethyl-3-cephem-4-carboxylic acid | 0.8 | 3.1 | 6.2 | 6.2 | 6.2 | 6.2 | >200 | 12.5 | 3.1 |
| 7β-(1,3,4-thiadiazol-2-yl)thioacetamido-7α-methoxy-3-(1-methyl-1H-tetrazol-5-yl)thiomethyl-3-cephem-4-carboxylic acid | 0.4 | 0.8 | 1.5 | 1.5 | 1.5 | 1.5 | >200 | 3.1 | 0.8 |
| 7β-(3-isoxazolyloxy)acetamido-7α-methoxy-3-(1-methyl-1H-tetrazol-5-yl)thiomethyl-3-cephem-4-carboxylic acid | 0.2 | 0.8 | 3.1 | 3.1 | 3.1 | 3.1 | >400 | 6.2 | 1.5 |
| 7β-propargylthioacetamido-7α-methoxy-3-(1-methyl-1H-tetrazol-5-yl)thiomethyl-3-cephem-4-carboxylic acid | 0.2 | 0.8 | 3.1 | 3.1 | 3.1 | 3.1 | 400 | 3.1 | 0.8 |
| 7β-cyanomethylthioacetamido-7α-methoxy-3-(1-methyl-1H-tetrazol-5-yl)thiomethyl-3-cephem-4-carboxylic acid | 0.2 | 0.8 | 0.8 | 0.8 | 0.8 | 0.8 | >200 | 1.5 | 0.2 |
| 7β-(5-methyl-1,3,4-thiadiazol-2-yl)thioacetamido-7α-methoxy-3-(1-methyl-1H-tetrazol-5-yl)thiomethyl-3-cephem-4-carboxylic acid | 0.4 | 1.5 | 12.5 | 12.5 | 6.2 | 12.5 | 400 | 3.1 | 1.5 |
| 7β-(1,2,4-triazol-4H-3-yl)thioacetamido-7α-methoxy-3-carbamoyloxymethyl-3-cephem-4-carboxylic acid | 1.5 | 6.2 | 6.2 | 12.5 | 12.5 | 6.2 | >400 | 25 | 6.2 |
| 7β-(imidazol-2-yl)thioacetamido-7α-methoxy-3-carbamoyloxymethyl-3-cephem-4-carboxylic acid | 0.1 | 0.8 | 1.5 | 3.1 | 3.1 | 3.1 | >200 | 6.2 | 1.5 |
| 7β-(1,3,4-thiadiazol-2-yl)thioacetamido-7α-methoxy-3-carbamoyloxymethyl-3-cephem-4-carboxylic acid | 0.4 | 1.5 | 3.1 | 3.1 | 3.1 | 3.1 | >400 | 6.2 | 1.5 |
| 7β-(5-methyl-1,3,4-thiadiazol-2-yl)thioacetamido-7α-methoxy-3-carbamoyloxymethyl-3-cephem-4-carboxylic acid | 0.8 | 3.1 | 6.2 | 6.2 | 12.5 | 6.2 | >200 | 6.2 | 3.1 |
| 7β-propargylthioacetamido-7α-methoxy-3-carbamoyloxymethyl-3-cephem-4-carboxylic acid | 0.8 | 1.5 | 3.1 | 3.1 | 6.2 | 3.1 | >400 | 6.2 | 1.5 |
| 7β-cyanomethylthioacetamido-7α-methoxy-3-carbamoyloxymethyl-3-cephem-4-carboxylic acid | 0.8 | 1.5 | 1.5 | 0.8 | 3.1 | 0.4 | >400 | 6.2 | 0.4 |
| 7β-cyanomethylthioacetamido-7α-methoxy-3-acetoxymethyl-3-cephem-4-carboxylic acid | 0.2 | 0.8 | 1.5 | 1.5 | 3.1 | 1.5 | >400 | 6.2 | 0.8 |
| 7β-azidomethylthioacetamido-7α-methoxy-3-acetoxymethyl-3-cephem-4-carboxylic acid | 0.4 | 0.8 | 6.2 | 6.2 | 6.2 | 6.2 | >200 | 3.1 | 1.5 |
| 7β-(1,3,4-thiadiazol-2-yl)thioacetamido-7α-methoxy-3-acetoxymethyl-3-cephem-4-carboxylic acid | 0.8 | 1.5 | 3.1 | 6.2 | 6.2 | 3.1 | >400 | 6.2 | 3.1 |
| 7β-propargylthioacetamido-7α-methoxy-3-acetoxymethyl-3-cephem-4-carboxylic acid | 0.8 | 3.1 | 3.1 | 6.2 | 6.2 | 6.2 | >400 | 6.2 | 1.5 |
| 7β-(imidazol-2-yl)thioacetamido-7α-methoxy-3-acetoxymethyl-3-cephem-4-carboxylic acid | 1.5 | 6.2 | 12.5 | 25 | 25 | 12.5 | >400 | 25 12 | 6.2 |
| 7β-(3-isoxazolyloxy)acetamido-7α-methoxy-3-acetoxymethyl-3-cephem-4-carboxylic acid | 0.1 | 0.8 | 6.2 | 6.2 | 12.5 | 6.2 | >400 | 12.5 | 3.1 |
| 7β-(3-isoxazolyl)thioacetamido-7α-methoxy-3-acetoxymethyl-3-cephem 4-carboxylic acid | 0.2 | 0.8 | 3.1 | 6.2 | 6.2 | 3.1 | >400 | 3.1 | 1.5 |
| 7β-methylsulfonylacetamido-7α-methoxy-3-(1-methyl-1H-tetrazole-5-yl)thio- | 0.8 | 3.1 | 1.5 | 1.5 | 1.5 | 0.8 | 400 | 12.5 | 0.4 |

Table-continued

| Tested compounds | Minimal inhibitory concentrations of various microorganisms mcg/ml | | | | | | | | |
|---|---|---|---|---|---|---|---|---|---|
| | I* | | II | | III | IV | | V | VI |
| | A | B | A | B | | A | B | | |
| methyl-3-cephem-4-carboxylic acid | | | | | | | | | |

*I A: *Staphylococcus aureus* 209p
I B: *Staphylococcus aureus* (CP and PC resistant)
II A: *E. coli* NIHJ
II B: *E. coli* 609 (CER resistant)
III: *Shigella flexneri* Komagome
IV A: *Klebsiella neumoniae* 806
IV B: *Klebsiella neumoniae* 846 (CER resistant)
V: *Proteus vulgaris*
VI: *Salmonella enteritidis* Gaertner As shown above, the compounds obtained by this invention have excellent antimicrobial activities against broad pathogenic microogranisms. These compounds can be administered orally or parenterally, for example, in the shape of capsules, tablets, and injections and most preferably by means of injection. The dosage unit depends upon the age, disease and weight of the patients, but a usual dosage unit is in amounts of from 100 to 3,000 mg/per day and it is administered three or four times a day. But, if necessary, more than the above amount can be used.

This invention is illustrated in detail by the following examples, but these examples are not to be construed as limiting the scope of the invention.

EXAMPLE 1

Methyl 7β-phenoxyacetamido-7α-methoxy-3-methyl 3-cephem-4-carboxylate

To 180 mg of phosphorus pentachloride in 12 ml of chloroform 0.13 ml of quinoline was added. After several minutes, 200 mg of methyl 7-phenoxyacetamido-3-methyl-3-cephem-4-carboxylate was added thereto and the mixture was stirred at room temperature for 1 hour. After the solvent was distilled off under reduced pressure, 20 ml of anhydrous tetrahydrofuran was added to the residue and the appeared crystals were filtered off. To the filtrate 0.07 ml of triethylamine was added and the mixture was stirred at room temperature for 10 minutes and was cooled to −50° C and 1 ml of tetrahydrofuran containing 0.026 ml of bromine (0.5 m mole) was added dropwise thereto and stirred at −50° C for 10 minutes. Then the mixture was cooled to −78° C and a methanol solution of lithium methoxide made from 45 mg of metallic lithium and 3 ml of methanol was added at −78° C and stirred at the same temperature for 30 minutes. Then 0.41 ml of acetic acid was added to the mixture to cease the reaction. The reaction mixture was poured into water and extracted with ethyl acetate. The extract was washed with water and dried and the solvent was distilled under reduced pressure to give a residue, which was dissolved in 5 ml of chloroform. 0.1 ml of quinoline and 0.5 ml of trimethylchlorosilane were added to the solution and the mixture was stirred at room temperature overnight. The reaction mixture was poured into water and extracted with chloroform. The extract was washed with water dried and the solvent was distilled off under reduced pressure. The residue was purified by silica gel chromatography to give methyl 7β-phenoxyacetoamido-7α-methoxy-3-methyl-3-cephem-4-carboxylate.

NMR spectrum (CDCl$_3$) δ ppm; 2.17 (3H, singlet); 3.17 (2H, singlet); 3.55 (3H, singlet); 3.83 (3H, singlet); 4.59 (2H, singlet); 5.06 (1H, singlet); 6.8 − 7.5 (5H, multiplet).

EXAMPLE 2

Benzhydryl 7α-phenoxyacetamido-7α-methoxy-3-methyl-3-cephem-4-carboxylate

To 180 ml of phosphorus pentachloride in 12 ml of chloroform 0.13 ml of quinoline was added. After several minutes, 257 mg of benzhydryl 7-phenoxyacetamido-3-methyl-3-cephem-4-carboxylate was added thereto and the mixture was stirred at room temperature for one hour. Then the solvent was distilled under reduced pressure. 20 ml of anhydrous tetrahydrofuran was added to the residue and the appeared crystals were filtered off. To the filtrate 0.07 ml of triethylamine was added and the mixture was stirred at room temperature for 10 minutes and then cooled to −50° C. 1 ml of tetrahydrofuran containing 0.026 ml of bromine (0.5 m mole) was added thereto. After being stirred at −50° C for 10 minutes, the mixture was cooled to −78° C and a methanolic solution of lithium methoxide made from 45 mg of metallic lithium and 3 ml of methanol was added thereto. The mixture was stirred at the same temperature for 30 minutes and then 0.4 ml of acetic acid was added to cease the reaction. The reaction mixture was poured into water and the mixture was extracted with ethyl acetate. The extract was washed with water, dried and distilled under reduced pressure. The obtained residue was dissolved in 5 ml of chloroform and 0.1 ml of quinoline and 0.5 ml of trimethylchlorosilane were added and the mixture was stirred at room temperature overnight. The reaction mixture was poured into water and extracted with chloroform. The extract was washed with water and dried and the solvent was distilled off under reduced pressure. The obtained residue was purified by silica gel chromatography to give benzhydryl 7β-phenoxyacetamido-7β-methoxy-3-methyl-3-cephem-4-carboxylate.

IR spectrum $\nu_{max}^{liquid}$ cm$^{-1}$: 3300, 1780, 1735, 1700.

EXAMPLE 3

Methyl 7β-(α-thienylacetamido)-7α-methoxy-3-acetoxymethyl-3-cephem-4-carboxylate To 12 ml of chloroform solution containing 180 mg of phosphorus pentachloride 0.13 ml of quinoline was added. After several minutes, 410 mg of methyl 7-(α-thienylacetamido)-3-acetoxymethyl-3-cephem-4-carboxylate was added thereto ad the reaction mixture was stirred at room temperature for one hour and the solvent was distilled off under reduced pressure. 40 ml of anhydrous tetrahydrofuran was added to the residue and the appeared crystals were filtered off. To the filtrate 0.14 ml of triethylamine was added and the mixture was stirred at room temperature for 10 minutes and then cooled to −50° C. 2 ml of tetrahydrofuran solution of 0.052 ml (1 m mole) of bromine was added dropwise and stirred at −50° C for 10 minutes and then cooled to −78° C. A methanolic solution of lithium methoxide made from 100 mg of metallic lithium and 4 ml of methanol was added to the mixture at −78° C and stirred at the same temperture for 30 minutes. Then 1 ml of acetic acid was added to cease the reaction. The reaction mixture was poured into water and extracted with ethyl acetate. The extract was washed with water and dried and the solvent was distilled under reduced pressure. The obtained residue was dissolved into 10 ml of chloroform and 0.2 ml of quinoline and 1 ml of trimethylchlorosilane were added to the solution and the mixture was stirred at room temperature overnight. The reaction mixture was poured into water and extracted with chloroform. The extract was washed with water and dried and then distilled off under reduced pressure. The obtained residue was purified by silica gel chromatography to give methyl 7β-(α-thienylacetamido)-7α-methoxy-3-acetoxymethyl-3-cephem-4-carboxylate.

IR spectrum $\nu_{max}^{Nujol}$ cm$^{-1}$: 3300, 1780, 1740, 1700. NMR spectrum (CDCl$_3$) δ ppm: 2.00 (3H, singlet); 3.23 and 3.43 (2H, AB quartet, J = 18Hz); 3.42 (3H, singlet); 3.77 (3H, singlet); 3.84 (2H, singlet); 4.76 and 4.85 (2H, AB quartet, J = 14Hz); 5.03 (1H, singlet); 6.8 – 8.2 (3H and 1H, multiplet).

EXAMPLE 4

Benzhydryl 7β-(α-thienylacetamido)-7α-methoxy-3-acetoxymethyl-3-cephem-4-carboxylate To 12 ml of chloroform solution containing 180 mg of phosphorus pentachloride 0.13 ml of quinoline was added. After several minutes, 281 mg of benzhydryl 7-(α-thienylacetamido)-3-acetoxymethyl-3-cephem-4-carboxylate was added thereto and the mixture was stirred at room temperature for 1 hour and the solvent was distilled off under reduced pressure. 20 ml of anhydrous tetrahydrofuran was added to the residue and the appeared crystals was filtered off. To the filtrate 0.07 ml of triethylamine was added and the mixture was stirred at room temperature for 10 minutes and then cooled to −50° C. 1 ml of tetrahydrofuran solution containing 0.026 ml (0.5 m mole) of bromine was added dropwise to the solution. The solution was stirred at −50° C for 10 minutes and then cooled at −78° C. A methanolic solution of lithium methoxide made from 45 mg of metallic lithium and 3 ml of methanol was added at −78° C to the solution and stirred at the same temperature for 30 minutes and 0.4 ml of acetic acid was added to cease the reaction. The reaction mixture was poured into water and extracted with ethyl acetate. The extract was washed with water, dried and distilled under reduced pressure. The obtained residue was dissolved in 5 ml of chloroform and 0.1 ml of quinoline and 0.5 ml of trimethylchlorosilane were added thereto and the mixture was stirred at room temperature overnight. The reaction mixture was poured into water and extracted with chloroform. The extract was washed with water, dried and the solvent was distilled off under reduced pressure. The obtained residue was purified by silica gel chromatography to give benzhydryl 7β-(α-trienylacetamido)-7α-methoxy-3-acetoxymethyl-3-cephem-4-carboxylate.

IR spectrum $\nu_{max}^{liquid}$ cm$^{-1}$: 3300, 1780, 1740, 1700. NMR spectrum (CDCl$_3$) δ ppm; 1.95 (3H, singlet); 3.15 and 3.45 (2H, AB quartet, J = 18Hz); 3.39 (3H, singlet); 3.77 (2H, singlet); 4.72 and 4.96 (2H, AB quartet, J = 14Hz); 4.96 (1H, singlet); 6.8 – 6.9 (3H, multiplet); 7.20 (11 H).

Example 5

Methyl 7β-methylthioacetamido-7α-methoxy-3-methyl-3-cephem-4-carboxylate

To 12 ml of chloroform solution containing 180 mg of phosphorus pentachloride 0.13 ml of quinoline was added. After several minutes, 158 mg of methyl 7-methylthioacetamido-3-methyl-3-cephem-4-carboxylate was added to the solution and the mixture was stirred at room temperature for one hour and the solvent was distilled off under reduced pressure, 20 ml of anhydrous tetrahydrofuran was added to the residue and the appeared crystals were filtered off. To the filtrate 0.07 ml of triethylamine was added and the mixture was stirred at room temperature for 10 minutes and then cooled to −50° C. 1 ml of tetrahydrofuran solution containing 0.026 ml (0.5 m mole) of bromine was added dropwise. The solution was stirred at −50° C for 10 minutes and then cooled to −78° C. A methanolic solution of lithium methoxide made from 45 mg of metallic lithium and 3 ml of methanol was added at −78° C to the above solution and stirred at the same temperature for 30 minutes. Then 0.4 ml of acetic acid was added to the solution to cease the reaction. The reaction mixture was poured into water and extracted with ethyl acetate. The extract was washed with water and dried and distilled under reduced pressure. The obtained residue was dissolved in 5 ml of chloroform and 0.1 ml of quinoline and 0.5 ml of trimethylchlorosilane were added thereto. The mixture was stirred at room temperature overnight. The mixture was poured into water and extracted with ethyl acetate. The extract was washed with water, dried and distilled under reduced pressure. The residue was purified by silica gel chromatography to give methyl 7β-methylthioacetamido-7α-methoxy-3-methyl-3-cephem-4-carboxylate.

IR spectrum $\nu_{max}^{liquid}$ cm$^{-1}$: 1780, 1740, 1705.

EXAMPLE 6

Methyl 7β-phenylthioacetamido-7α-methoxy-3-methyl-3-cephem-4-carboxylate

To 12 ml of chloroform solution containing 180 mg of phosphorus pentachloride 0.13 ml of quinoline was added. After several minutes, 189 mg of methyl 7-phenylthioacetamido-3-methyl-3-cephem-4-carboxylate was added thereto and the mixture was stirred at room temperature for 1 hour and then the solvent was distilled under reduced pressure. 20 ml of anhydrous tetrahydrofuran was added to the residue and the appeared crystals were filtered off. To the filtrate 0.07 ml of triethylamine was added and the solution was stirred at room temperature for 10 minutes and then cooled to −50° C. 1 ml of tetrahydrofuran solution containing 0.026 ml (0.5 m mole) of bromine was added dropwise to the above solution and stirred at −50° C for 10 minutes and then cooled to −78° C. A methanolic solution of lithium methoxide made from 45 mg of metallic lithium and 3 ml of methanol was added at −78° C to the solution and stirred at the same temperature for 30 minutes. Then 0.4 ml of acetic acid was added thereto to cease the reaction. The reaction mixture was poured into water and extracted with ethyl acetate. The extract was washed with water, dried and then the solvent was distilled under reduced pressure. The residue was dissolved in 5 ml of chloroform and 0.1 ml of quinoline and 0.5 ml of trimethylchlorosilane were added and the mixture was stirred at room temperature overnight. The reaction mixture was poured into water and extracted with chloroform. The extract was washed with water and dried and the solvent was distilled off under reduced pressure. The obtained residue was purified by silica gel chromatography to give methyl 7β-phenylthioacetamido-7α-methoxy-3-methyl-3-cephem-4-carboxylate.

IR spectrum $\nu_{max}^{liquid}$ cm$^{-1}$: 1780, 1740, 1700

EXAMPLE 7

Benzhydryl 7β-cyanomethylthioacetamido-7α-methoxy-3-acetoxymethyl-3-cephem-4-carboxylate To 12 ml of chloroform solution containing 180 mg of phosphorus pentachloride 0.13 ml of quinoline was added. After several minutes, 275 mg of benzhydryl 7-cyanomethylthioacetamido-3-acetoxymethyl-3-cephem-4-carboxylate was added thereto and the mixture was stirred at room temperature for 1 hour and the solvent was distilled under reduced pressure. 20 ml of anhydrous tetrahydrofuran was added to the residue and the appeared crystals were filtered off. To the filtrate 0.07 ml of triethylamine was added and the mixture was stirred at room temperature and then cooled to −50° C. 1 ml of tetrahydrofuran solution containing 0.026 ml (0.5 m mole) of bromine was added dropwise to the above solution. The solution was stirred at −50° C for 10 minutes and then cooled to −78° C. A methanolic solution of lithium methoxide made from 45 mg of metallic lithium and 3 ml of methanol was added at −78° C to the solution and stirred at the same temperature for 30 minutes. Then 0.4 ml of acetic acid was added thereto to cease the reaction. The reaction mixture was poured into water and extracted with ethyl acetate. The extract was washed with water, dried and distilled under reduced pressure. The obtained residue was dissolved in chloroform and 0.1 ml of quinoline and 0.5 ml of trimethylchlorosilane was added thereto and the mixture was stirred at room temperature overnight. The reaction mixture was poured into water and extracted with ethyl acetate. The extract was washed with water, dried and the solvent was distilled off under reduced pressure. The obtained residue was purified by silica gel chromatography to give benzhydryl 7β-cyanomethylthioacetamido-7α-methoxy-3-acetoxymethyl-3-cephem-4-carboxylate.

NMR spectrum (CBCl$_3$)δ ppm
2.00 (3H, singlet);
3.3 - 3.5 (2H, AB aquartet, J = 18Hz);
3.41 (2H, singlet);
3.50 (2H, singlet);
3.55 (3H, singlet);
4.80 and 5.08 (AB quartet, J =14Hz);
5.10 (1H, singlet);
6.99 (1H, singlet);
7.39 (10 H).

Example 8

Methyl 7β-phenylacetamido-7α-methoxy-3-methyl-3-cephem-4-carboxylate

To 12 ml of chloroform solution containing 180 mg of phosphorus pentachloride 0.13 ml of quinoline was added. After several minutes, 173 mg of methyl 7-phenylacetamido-3-methyl-3-cephem-4-carboxylate was added thereto and the mixture was stirred at room temperature for one hour and the solvent was distilled under reduced pressure. 20 ml of anhydrous tetrahydrofuran was added to the residue and the appeared crystals were filtered off. To the filtrate 0.07 ml of triethylamine was added and the mixture was stirred at room temperature for 10 minutes and then cooled to −25° C. 1 ml of tetrahydrofuran solution containing 0.026 ml (0.5 m mole) of bromine was added dropwise to the solution. The solution was stirred at −25° C for 10 minutes and then cooled to −78° C. A methanolic solution of lithium methoxide made from 45 mg of metallic lithium and 3 ml of methanol was added to the solution at −78° C and stirred at the same temperature. Then 0.4 ml of acetic acid was added thereto to cease the reaction. The reaction mixture was poured into water and extracted with ethyl acetate. The extract was washed with water, dried and distilled under reduced pressure. The obtained residue was dissolved in 5 ml of chloroform and 1 ml of trifluoroacetic acid was added thereto and the mixture was stirred at room temperature for 20 minutes. The mixture was distilled under reduced pressure. To the obtained residue a phosphoric acid buffer solution (pH8) was added ad extracted with ethyl acetate. The extract was washed with water, dried and the solvent was distilled off under reduced pressure. The obtained residue was purified by silica gel chromatography to give methyl 7β-phenylacetamido-7α-methoxy-3-methyl-3-cephem-4-carboxylate.

IR spectrum $\nu_{max}^{liquid}$ cm$^{-1}$: 1780, 1740, 1700

EXAMPLE 9

Benzhydryl 7α-cyanomethylthioacetamido-7α-methoxy-3-(1-methyl-1H-tetrazol-5-yl)thiomethyl-3-cephem-4-carboxylate To 12 ml of chloroform solution containing 180 mg of phosphorus pentachloride 0.13 ml of quinoline was added. After several minutes, 304 mg of benzhydryl 7-cyanomethylthioacetamido-3-(1-methyl-1H-tetrazol-5-yl)thiomethyl-3-cephem-4-carboxylate was added thereto and the mixture was stirred at room temperature for 1 hour and the solvent was distilled under reduced pressure. 20 ml of anhydrous tetrahydrofuran was added to the residue and the appeared crystals were filtered off. To the filtrate 0.07 ml of triethylamine was added and the mixture was stirred at room temperature for 10 minutes and then cooled to −50° C. 1 ml of tetrahydrofuran solution containing 0.026 ml (0.5 m mole) of bromine was added dropwise to the solution. The solution was stirred at −50° C for 10 minutes and then cooled to −78° C. A methanolic solution of lithium methoxide made from 45 mg of metallic lithium and 3 ml of methanol was added to the above solution at −78° C and the mixture was stirred at the same temperature for 30 minutes. Then 0.4 ml of acetic acid was added thereto to cease the solution. The reaction mixture was poured into water and extracted with ethyl acetate. The extract was washed with water, dried and the solvent was distilled off under reduced pressure. The residue was dissolved in 5 ml of chloroform, and 0.1 ml of quinoline and 0.5 ml of trimethylchlorosilane were added to the solution and the solution was stirred at room temperature overnight. The reaction mixture was poured into water and extracted with chloroform. The extract was washed with water, dried and the solvent was distilled off under reduced pressure. The obtained residue was purified by silica gel chromatography to give benzhydryl 7β-cyanomethylthioacetamido-7α-methoxy-3-(1-methyl-1H-tetrazol-5-yl)thiomethyl-3-cephem-4-carboxylate.

NMR spectrum (CDCl$_3$) δ ppm: 3.44 (2H, singlet); 3.49 (2H, singlet); 3.55 (3H, singlet); 3.60 (2H, singlet); 3.82 (3H, singlet); 4.25 and 4.48 (2H, AB quartet); 5.06 (1H, singlet); 6.93 (1H, singlet); 7.38 (10 H).

What is claimed is:

1. A process for preparing a cephalosporin derivative having the formula

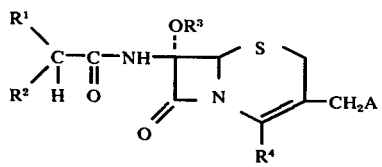

Wherein R$^1$ represents hydrogen, alkyl having 1 – 4 carbon atoms, phenyl or naphthyl; R$^2$ is hydrogen, alkyl having 1 – 4 carbon atoms, phenyl or napthyl, alkylthio having 1 – 4 carbon atoms, alkynylthio having 2 – 4 carbon atoms, phenylthio, azidoalkylthio having 1 – 4 carbon atoms, cyanoalkylthio having 1 – 4 carbon atoms in the alkyl moiety, alkylsulfonyl having 1 – 4 carbon atoms, 5- or 6-membered heterocyclic optionally substituted with a lower alkyl having from 1 to 3 carbons and selected from the group consisting of thienyl, imidazolyl, thiadiazolyl, isoxazolyl, tetrazolyl, pyrimidinyl and pyridyl, 5- or 6-membered heterocyclic thio optionally substituted with a lower alkyl having from 1 to 3 carbons and selected from the group consisting of imidazolylthio, thiadiazolylthio, triazolythio, thienylthio, isoxazolylthio, tetrazolythio, pyrimidinylthio and pyridylthio, or 5-or 6-membered heterocyclic oxy optionally substituted with a lower alkyl having from 1 to 3 carbon atoms and selected from the group consisting of isoxazolyloxy, imidazolyloxy, thiadiazolyloxy, triazolyloxy, thienyloxy, tetrazolyloxy, pyrimidinyloxy and pyridyloxy; R$^3$ is alkyl having 1 –4 carbon atoms; R$^4$ is carboxyl, alkoxycarbonyl having 1 – 4 carbon atoms in the alkyl moiety, chloroalkoxycarbonyl having 1 – 4 carbon atoms in the alkyl moiety, benzyloxycarbonyl optionally substituted with methoxy or nitro, diphenylmethyloxycarbonyl, trialkylsilyloxycarbonyl having 1 – 4 carbon atoms in each alkyl moiety, dialkylhalogenosilyloxycarbonyl having 1 – 4 carbon atoms in each alkyl moiety wherein halogen is chloro or bromo, phenacyloxycarbonyl optionally substituted with halogen or methoxy, acetoxycarbonyl, benzoyloxycarbonyl, chloroacetoxycarbonyl, bromoacetoxycarbonyl, dichlorophosphinooxycarbonyl, dibromophosphinooxycarbonyl, dimethylphosphinooxycarbonyl or an aminocarbonyl; A is hydrogen, azido or the formula —B—E wherein B is oxygen or sulfur and E is acetyl, propionyl or benzoyl, alkyl having 1 – 4 carbon atoms or optionally substituted - carbamoyl, - thiocarbamoyl or - heterocyclic group which comprises contacting a 7β-acylaminocephalosporin having the formula:

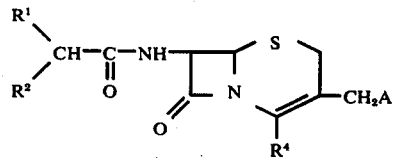

wherein R$^1$, R$^2$, R$^4$ and A have the same meansings as above with a halogenating agent selected from the group consisting of a phosphorus halide and a halogenated sulfur compound to form an iminohalide having the formula:

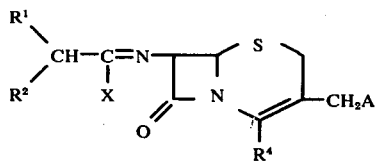

wherein X represents a halogen atom and R$^1$, R$^2$, R$^4$ and A have the same meanings as above, contacting the said iminohalide with a base selected from the group consisting of an alkali metal carbonate, alkali metal hydroxide, an organic tertiary amine, diazabicyclooctane and diazabicyclononene, to form a keteneimine having the formula:

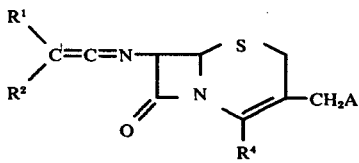

Wherein R$^1$, R$^2$, R$^4$ and A have the same meanings as above, contacting the said keteneimine with a halogen selected from the group consisting of chlorine, bromine and iodine, to form a halogeno-iminohalide having the formula:

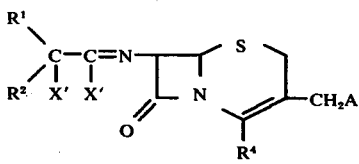

wherein R$^1$, R$^2$, R$^4$ and A have the same meanings as above and X' represents a halogen atom, contacting the said halogeno-iminohalide with an alkali metal alkoxide having the formula:

R$^3$OM wherein M represents an alkali metal and R$^3$ has the same meaning as above, and consecutively either subjecting the resulting compound to hydrolysis in the presence of water or an acid selected from the group consisting of hydrochloric acid, sulfuric acid, trifluoroacetic acid and trichloroacetic acid, or contacting the resulting compound with said acid or a chlorosilyl compound, followed by contacting the resulting compound with water.

2. The process of claim 1, in which halogenoiminohalide is contacted with the alkali metal alkoxide and the resulting compound is contacted with a chlorosilyl compound followed by contacting the resulting compound with water.

3. The process of claim 2 in which the alkali metal alkoxide is lithium methoxide.

4. The process of claim 2 in which the chlorosilyl compound is a dialkyldichlorosilane or a trialkylchlorosilane.

5. The process of claim 4 in which the trialkylhalogenosilane is trimethylchlorosilane.

6. The process of claim 1, in which the halogenoiminohalide is contacted with the alkali metal alkoxide and the resulting compound is contacted with said acid followed by contacting the resulting compound with water.

7. The process of claim 6 in which the acid is trifluoroacetic acid.

* * * * *

UNITED STATES PATENT AND TRADEMARK OFFICE
CERTIFICATE OF CORRECTION

PATENT NO. : 4,017,488
DATED : April 12, 1977
INVENTOR(S) : TETSUO HIRAOKA et al It is certified that error appears in the above-identified patent and that said Letters Patent are hereby corrected as shown below:

Column 1, line 10, formula (I): replace the formula with

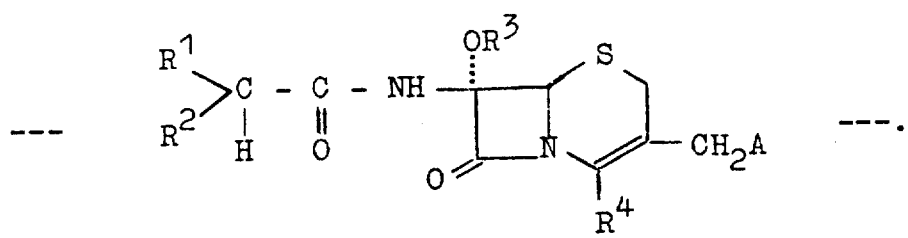

Column 3, line 15, formula (III): replace the formula with

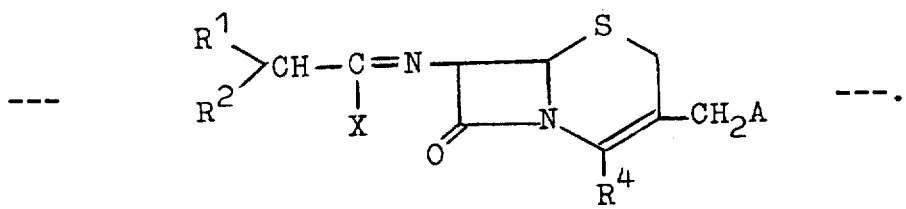

UNITED STATES PATENT AND TRADEMARK OFFICE
CERTIFICATE OF CORRECTION

PATENT NO. : 4,017,488
DATED : April 12, 1977
INVENTOR(S) : TETSUO HIRAOKA et al It is certified that error appears in the above-identified patent and that said Letters Patent are hereby corrected as shown below:

Column 2, line 63: delete "the" (first occurrence).

Column 2, line 63: replace "-alkoxycephalosparine" with --- -alkoxycephalosporins ---.

Column 3, line 63: before "cephalosporin", replace "the" with --- a ---.

Column 4, line 18: insert a comma (,) after --- methylenechloride ---.

Column 4, line 39: after "resulting", insert --- from ---.

Column 5, line 13: insert --- the --- after "into".

Column 7, in the Table, second column: at lines 8 and 18, before "0.1", insert --- $\leq$ ---.

Column 10, line 53: replace "7β-methoxy-" with --- 7α-methoxy- ---.

Column 10, line 66: replace "ad" with --- and ---.

Column 14, line 35: replace "ad" with --- and ---.

UNITED STATES PATENT AND TRADEMARK OFFICE
CERTIFICATE OF CORRECTION

PATENT NO. : 4,017,488

DATED : April 12, 1977

INVENTOR(S) : TETSUO HIRAOKA et al

It is certified that error appears in the above-identified patent and that said Letters Patent are hereby corrected as shown below:

Column 14, line 45: replace "7α-cyano" with --- 7β-cyano ---.

Column 16, line 15: replace "meansings" with --- meanings ---.

*Signed and Sealed this*

*Eighteenth* Day of *October 1977*

[SEAL]

Attest:

RUTH C. MASON
*Attesting Officer*

LUTRELLE F. PARKER
*Acting Commissioner of Patents and Trademarks*